(12) United States Patent
Baumann et al.

(10) Patent No.: US 11,786,115 B2
(45) Date of Patent: Oct. 17, 2023

(54) METHOD AND APPARATUS TO GENERATE HYPERSPECTRAL IMAGE DATA WITH A MEDICAL IMAGING DEVICE

(71) Applicant: KARL STORZ SE & Co KG, Tuttlingen (DE)

(72) Inventors: Harald Baumann, Tuttlingen (DE); Christin Baumann, Tuttlingen (DE)

(73) Assignee: KARL STORZ SE & Co KG, Tuttlingen (DE)

( * ) Notice: Subject to any disclaimer, the term of this patent is extended or adjusted under 35 U.S.C. 154(b) by 0 days.

(21) Appl. No.: 17/957,652

(22) Filed: Sep. 30, 2022

(65) Prior Publication Data
US 2023/0035614 A1 Feb. 2, 2023

Related U.S. Application Data

(63) Continuation of application No. 17/187,338, filed on Feb. 26, 2021, now Pat. No. 11,553,837.

(30) Foreign Application Priority Data

Mar. 2, 2020 (DE) .......................... 102020105459.9

(51) Int. Cl.
*A61B 1/04* (2006.01)
*H04N 7/18* (2006.01)
(Continued)

(52) U.S. Cl.
CPC ............ *A61B 1/043* (2013.01); *A61B 1/0005* (2013.01); *A61B 1/00009* (2013.01);
(Continued)

(58) Field of Classification Search
CPC ... A61B 1/043; A61B 1/00009; A61B 1/0005; A61B 1/00096; A61B 1/045;
(Continued)

(56) References Cited

U.S. PATENT DOCUMENTS

| 2010/0056928 | A1* | 3/2010 | Zuzak ....................... G01J 3/10 356/302 |
| 2014/0163319 | A1* | 6/2014 | Blanquart .......... G02B 23/2484 600/109 |

(Continued)

*Primary Examiner* — Nasim N Nirjhar
(74) *Attorney, Agent, or Firm* — David N. Villalpando

(57) ABSTRACT

Improved fluorescent imaging and other sensor data imaging processes, including hyperspectral imaging, devices, and systems are provided to enhance endoscopes with multiple wavelength capabilities and providing sequential imaging and display. A first optical device is provided for endoscopy imaging in a white light and a fluoresced light mode with an imaging unit including one or more image sensors. A mechanism in the first optical device to automatically adjust the focus of the first optical device using one or more deformable, variable-focus lenses, wherein the automatic focus adjustment compensates for a chromatic focal difference between the light collected at distinct wavelength bands caused by the dispersive or diffractive properties of the optical materials or optical design employed in the construction of the first or second optical devices, or both. Further variable spectrum imaging is enhanced with the use of adjustable spectral filters.

7 Claims, 9 Drawing Sheets

(51) Int. Cl.
*A61B 1/00* (2006.01)
*A61B 1/045* (2006.01)
*A61B 1/06* (2006.01)
*H04N 23/56* (2023.01)
*H04N 23/80* (2023.01)
*H04N 23/50* (2023.01)

(52) U.S. Cl.
CPC .......... *A61B 1/00096* (2013.01); *A61B 1/045* (2013.01); *A61B 1/0638* (2013.01); *A61B 1/0646* (2013.01); *H04N 7/183* (2013.01); *H04N 23/56* (2023.01); *H04N 23/80* (2023.01); *H04N 23/555* (2023.01)

(58) Field of Classification Search
CPC .... A61B 1/0638; A61B 1/0646; H04N 7/183; H04N 23/56; H04N 23/80; H04N 23/555
See application file for complete search history.

(56) References Cited

U.S. PATENT DOCUMENTS

| | | | |
|---|---|---|---|
| 2017/0176338 A1* | 6/2017 | Wu | G02B 21/367 |
| 2019/0000308 A1* | 1/2019 | Duckett, III | A61B 1/00133 |
| 2019/0281204 A1* | 9/2019 | Darty | G01J 3/2823 |

* cited by examiner

METHOD AND APPARATUS TO GENERATE HYPERSPECTRAL IMAGE DATA WITH A MEDICAL IMAGING DEVICE

CROSS REFERENCE TO RELATED APPLICATIONS

This application is a continuation of U.S. patent application Ser. No. 17/187,338, filed Feb. 26, 2021, and entitled "Medical Imaging Device with Multiple Imaging Modes," now U.S. Pat. No. 11,553,837, issued on Jan. 17, 2023, which claims priority to German Application No. 102020105459.9 filed Mar. 2, 2020, entitled, "Medical Imaging Device with Multiple Imaging Modes," both disclosures are incorporated herein by reference.

FIELD OF THE INVENTION

The present invention relates to an observation instrument, particularly one in the field of endoscopy, and to a distally placed video imager arrangement for such an observation instrument. The invention relates generally to the field of image capture and more specifically to medical imaging camera heads, endoscopes, video endoscopes and camera designs capable of imaging in multiple spectra.

BACKGROUND OF THE INVENTION

Endoscopes for medical or non-medical applications generally employ an elongate shaft configured for being introduced into an internal cavity of a human or animal body or another object to be examined. In a distal (i.e. distant from a user) end section of the shaft imaging optics, such as an objective lens, may be arranged for collecting image light and generating an image of a subject scene in the cavity of the body or object. Further, the endoscope may have a handle attached to a proximal (i.e. close to a user) end section of the shaft. In video endoscopes, which also are denoted electronic endoscopes, the captured endoscopic image is picked up by one or more electronic image sensors. The image sensor (or sensors) may be located in the distal end of the shaft, as is common in endoscopes frequently referred to as "Chip on the tip" (COTT) endoscopes, or may be located in a camera head element, to which the shaft is attached, the collected image light being generally relayed from the distal end to the proximal end by optical elements, such as rod lenses.

Certain endoscopic observations may employ fluorescing agents or auto-fluorescence to better examine tissue. A fluorescing agent such as a dye may be injected or otherwise administered to tissue and an excitation light directed toward the tissue. Responsive to the excitation light, the fluorescing agent fluoresces (emits light typically at a longer wavelength than the excitation light), allowing an image sensor to detect the emitted light that is often in a wavelength not visible to the human eye. The detected images may be examined to indicate the concentration of fluorescing agent in the observed tissue. Further, a phenomenon known as autofluorescence may occur in which tissue fluoresces under certain conditions without a fluorescing agent. Such light can be detected as well. Images based on detected fluoresced light, known as "fluorescence imaging" (FI), are useful in medical diagnosis, testing, and other scientific fields.

In related technologies, European patent application EP3420880A1 discloses a fluorescence imaging scope with variable focusing structures for in-focus capture of image streams in the visible and infrared spectra ranges, obviating, thereby, the need to manually refocus the image subsequent to switching the illumination and viewing spectrum. European application EP1327414B1 describes a device for the imaging diagnosis of tissue, in which a degree of transmission of an illumination light can be adjusted by means of a variable spectral filter.

As mentioned above, a typical prior art endoscope generally includes a first imaging lens (e.g., an objective) which may be followed by a series of carrier lenses (e.g., relays) which capture and transmit an optical image from inside an enclosed area, generally of a human or animal body, to a region outside of the body. The proximal end of the endoscope may be attached, via direct coupling or an adaptor, to a camera head or an eye-piece for viewing. The camera head may include lenses for receiving the optical image and forming an optical image onto the image sensor. The digital image captured by the image sensor can then be transmitted to a camera control unit (CCU) or other similar imaging unit or module for analysis and display.

State of the art endoscopes used for fluorescent imaging (FI) applications, and particularly indocyanine green (ICG) applications, are frequently designed and deployed primarily for visible light imagery. To perform FI imaging, such scopes may employ an appropriate optical filter to block the stimulus light and transmit fluoresced light. Since these endoscopes are designed for use with visible light (wavelengths of approximately 450-650 nm), the infrared fluorescence (generally 800-900 nm) is focused in a different plane than the visible light. Therefore, in addition to adding a filter, the user must refocus when switching between visible light mode and fluorescence mode. Focal differences exist because the endoscopes are not chromatically corrected for the infrared where certain fluorescence bands (particularly those associated with ICG) are located. Such differences, even in the face of common correction techniques, often result in a signal to noise ratio of FI imaging being low, resulting in poor quality FI images. Given the dispersion characteristics of optical elements used in the endoscope's optical channel, such as rod lenses, correcting these issues may be difficult or expensive. For example, when autofocus algorithms are employed, the algorithm is frequently slow to apply the correction.

It is therefore an object of the present invention to provide an endoscope in which the above mentioned drawbacks are largely avoided. In particular, it is an object of the invention to provide devices and methods that enable an endoscopic system to compensate for the endoscope characteristics when detection mode is switched between white light fluorescence imaging, and to provide sequential imaging, processing and display of images captured in multiple spectra.

These objects are met by the invention.

The present invention, according to an aspect of the invention, relates to a medical imaging system with medical imaging device, generally an endoscope. The medical imaging device is operable to capture a first image of a subject scene in first finite wavelength band of light, and capture a second image of the subject scene in a second finite wavelength band of light. The first and second wavelength bands are not the same, that is, while there may be some overlap in the wavelengths of each band, they are not identical in range and/or value. The imaging device includes a first imaging lens to capture light from an illuminated subject scene and an imaging unit with one or more image sensors that may capture images in the first wavelength band and the second wavelength band. The medical imaging device also includes a deformable, variable focal length lens located upstream of the one or more of the image sensors. The deformable lens automatically adjusts, by means of adjustment control circuitry, the focus of the medical imaging device to compensate for chromatic focal difference between the light received by the one or more image sensors at the first wavelength band and light received by the one or more image sensors at the second wavelength band, the chromatic focal difference being a result of the dispersive or diffractive properties of optical materials or optical design employed in an assembly construction of the medical imaging device, resulting in images being captured in-focus regardless of the wavelength band of the collected image light. The medical imaging system also includes an image processor that receives a first image from the imaging unit and a second image from the imaging unit.

The image processor according to the present invention may be operative to form a composite image by combining portions of the first image and portions of the second image. Images collected in a wavelength region outside of the visible spectrum, may have portions thereof displayed, on an image display, in false color representations in the composite image, such as a composite overlay, with the non-visible light image overlaid, in false color, over the visible light image. According to preferred embodiments of the invention multiple frames at the first wavelength band and the second wavelength band may be displayed (or stored in a system memory) sequentially, resulting in a real time, or near-real time, video stream. In a most preferred embodiment, the frame rate of the video stream will be at least 10 frames per second (FPS), and more preferably 24 or 30 FPS, which are industry standards.

In another aspect of the invention, the light collected by the medical imaging device, such as a detachable or affixed endoscope, may be split upstream from the imaging unit, and the imaging unit may contain one sensor for each resultant split beam. In some embodiments, the beam splitter splits the incoming beam by wavelength, the resulting split beams having differing, non-overlapping wavelength bands. Along at least one of the resulting optical paths will be positioned the deformable lens, but in some embodiments both beam paths may have a deformable, variable focal length lens.

In another embodiment of the invention, which may be used in conjunction with other embodiments, the image sensor or sensors may include spectral filters as integral elements thereof, that is, individual pixels and/or groups of pixels of the image sensor may be covered by spectral filters.

In another aspect of the invention, the medical imaging device may include one or more variable band spectral filters, the spectral band passed by each spectral filter being determined by its angular position along its respective optical channel. In preferred embodiments with a beam splitter, each optical channel, may contain both a variable band spectral filter and a deformable, variable focal length lens, the deformable lens automatically correcting the focal length of the optical channel in response to the selected wavelength band passed by the respective filter, resulting in in-focus images collected by the respective image sensor for each collected image at each transmitted spectral band. In some embodiments, the position of the spectral filters may be controlled by a respective actuator.

According to another aspect of the invention, the medical imaging device is employed to generate sequential, composite image frames of a subject scene, where the composite image frame, generated by an image processor, is composed of an image captured in a visible spectrum and an image captured in a non-visible spectrum, the non-visible spectrum image may be represented on a display as a false-colored image overlaid on the visible spectrum image. In this aspect of the invention, an image scene may be illuminated with a first wavelength band of light, and the image light from the scene is collected by means such as a first imaging lens. The collected light passes through a deformable, variable-focal length lens and onto an image sensor. The focal length of the deformable lens is adjusted such that an image captured by image sensor is in-focus, and the captured image data for the visible spectrum image is transmitted to an image processor. Subsequently, the subject scene is illuminated with a second wavelength band of light selected to cause at least a portion of the subject scene to fluoresce, the resulting fluorescence image light being at least partially outside of the visible spectrum. The fluorescence image light is captured by the light collection means and passes through a deformable, variable focal length lens and onto the image sensor. The focal length of the deformable lens is adjusted such that an image captured by the image sensor is in-focus, and that captured image data for the fluorescence image is transmitted to the image processor. The image processor processes the received images, and the resulting composite image frames may be displayed sequentially on an image display and/or stored in a computer memory.

According to an inventive method, an inventive medical imaging device is employed to generate hyperspectral image data, such as a "hyperspectral cube," the hyperspectral image data including a plurality of individual video frames, each with image data collected at distinct and different finite wavelength bands. Each collected frame of the hyperspectral image data is captured by illuminating a subject scene with a finite wavelength band of light, collecting image light from the scene with a means such as an objective lens, the collected image light passing through a deformable, variable-focal length lens and onto an image sensor, and adjusting the focal length of the deformable lens such that a captured image is in-focus at the image sensor plane for the wavelength band of light captured. This captured frame is transmitted to an image processor where it may be combined with subsequent captured frames to generate hyperspectral image data. Subsequent frames are collected, and the collected wavelength band is varied by one or more of the methods described below.

In another aspect of this inventive method, the wavelength band of the subject scene illuminating light may be changed between each frame, and a corresponding focal length change may be made by adjusting the deformable lens, such that an in-focus image may be captured by the image sensor for each subsequent frame at the respective wavelength band.

In another aspect of this inventive method for generating hyperspectral image data, the wavelength band may be adjusted by providing a variable band-pass spectral filter upstream of the image sensor, the variable band-pass spectral filter passing only a fraction of the spectrum of light incident upon it to the image sensor. In one embodiment of the inventive method, the angular position of the spectral filter may be adjusted between frames, and a corresponding adjustment of the deformable lens may be made, resulting in an in-focus image at a second wavelength band being able to be captured by the image sensor.

In a preferred embodiment of the inventive method for generating hyperspectral image data, the collected image light may be split by wavelength range into a first beam with a first wavelength band and a second beam with a second wavelength band. Subsequent to splitting the beam, each resultant beam may be passed through a variable band-pass spectral filter and corresponding deformable, variable focal length lens to an image sensor. Between each collected frame, the angular position of the variable band-pass spectral filter for one or more of the optical channels may be changed and a corresponding change be made to the deformable lens in that optical channel, such that an in-focus image at the passed wavelength band may be captured at the respective image sensor. In a particularly preferred embodiment, the spectral filters and deformable lenses may be adjusted at approximately the same time, and thus images may be collected by both image sensors, resulting in two, independent frames being simultaneously captured at two distinct wavelength bands. Collected frame data may be transmitted to an image processing, display and/or storage unit.

In a preferred embodiment, the collected image light may be split by wavelength resulting in one beam of wavelengths less than 1000 nm and another beam with wavelengths greater than 1000 nm.

Further features of the endoscopic system are disclosed in the co-pending German Patent Application No. 102019134314.3, filed Dec. 13, 2019, and entitled "Medizinische Bildgebungsvorrichtung"; filed by the same applicant on the same day as the present application, which is hereby incorporated by reference into the present application.

The features of the invention as mentioned above and as described below apply not only in the combinations mentioned but also in other combinations or alone, without leaving the scope of the present invention.

Further aspects of the present invention will be apparent from the figures and from the description of particular embodiments that follow. These figures show examples of the invention. The figures, the description and the requirements contain numerous features in combination. One of skill in the art will recognize the features individually and combine them into meaningful further combinations.

DETAILED DESCRIPTION OF EXAMPLE EMBODIMENTS

Figure 1:
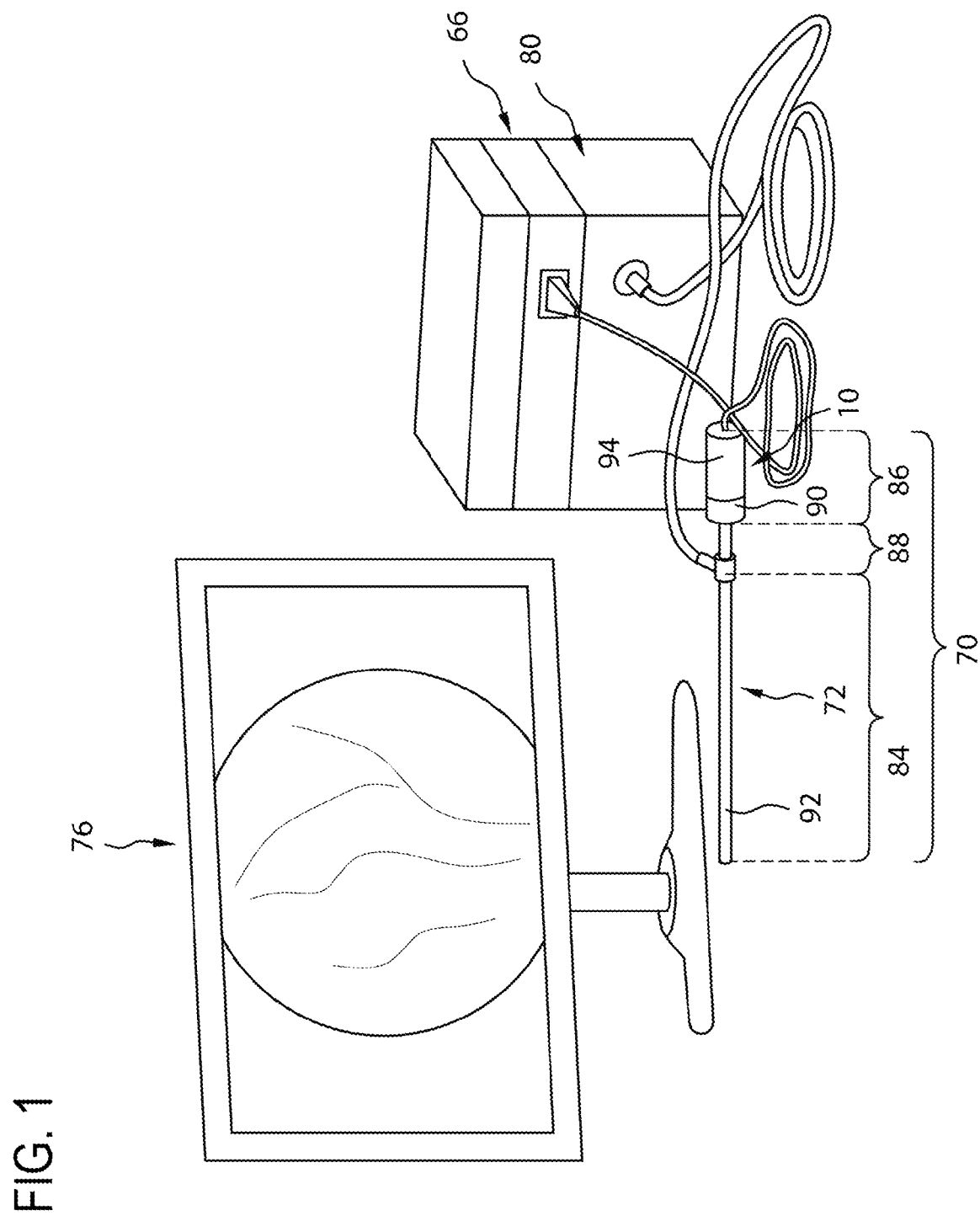
FIG. 1 shows a schematic representation of a medical imaging system in a perspective view.

FIG. 1 shows a schematic representation of a state-of the art medical imaging system in a perspective view. The medical imaging system in this case is an endoscopic imaging system. Alternatively, the medical imaging system could comprise an exoscopic, microscopic or macroscopic imaging system. The medical imaging system is intended to examine a cavity. The medical imaging system comprises at least one medical imaging device 70. The medical imaging device 70 in this case is an endoscope 72. Alternatively, the medical imaging device 70 could be an exoscope, a microscope and/or a macroscope. The medical imaging device 70 has a distal section 84 designed to be inserted into a cavity during an operation procedure. The distal section 84 faces the patient during the operation procedure and faces away from the operator. In addition, the medical imaging device 70 has a proximal section 86 located outside of the cavity of the operation procedure. The proximal section 86 faces away from a patient during the operation and faces towards the operator. The medical imaging device 70 has an intermediate section 88 located between distal section 84 and proximal section 86. The medical imaging device comprises a connection unit 90 located adjacent to intermediate section 88. The connector unit 90 is formed to connect the proximal portion 86 and the distal portion 84 to each other. In some embodiments the connection unit 90 is formed to provide a separable connection between the proximal portion 86 and the distal portion 84, such as a bayonet mount.

The medical imaging device 70 has at least one shaft 92. The shaft 92 forms at least partially the distal section 84 of the medical imaging device 70. The medical imaging device further comprises at least one handle 94. The handle 94 forms at least partially the proximal section 86 of the medical imaging device 70.

The medical imaging device 70 comprises at least one imaging unit 10. The imaging unit 10 may be located in the area of the proximal section 86 and be integrated into the handle 94. Alternatively, or additionally, the imaging unit 10 may be located at least partially in the distal section 84 area, in particular integrated into the shaft 92.

Figure 2:
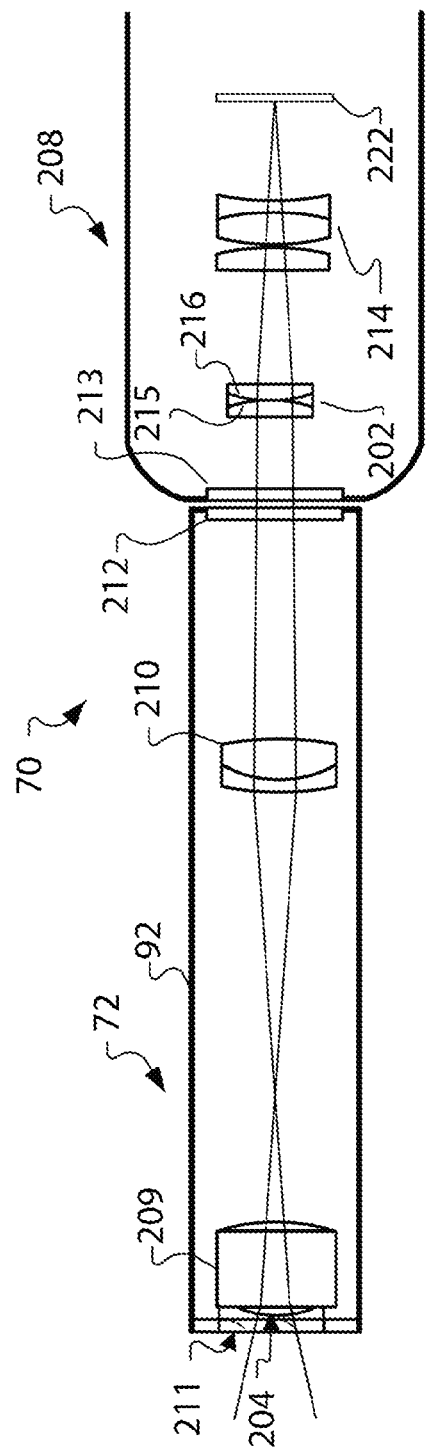
FIG. 2 shows a cross section diagram of a video endoscope device according to an example embodiment of the invention.

FIG. 2 shows cross section diagram of a video endoscope device 70 according to an example embodiment of the invention. This device 70 includes a first optical device 208 (in this version "camera head" 208 (which may correspond to imaging unit 10 of FIG. 1)) connected in a detachable manner as known in the art, such as with a bayonet mount, to endoscope 72 ("second optical device"). Endoscope 72 includes a shaft 92. Other versions may, of course, include a scope integrated with the camera head or in a single first optical device. Various structural components supporting the depicted elements are omitted in the figure, as well as other components such as illumination lights sources, fluorescent excitation light sources, optional relay optical elements, and controls, which are known in the art and are not shown in order to avoid obscuring the relevant details of the example embodiments of the invention.

Toward the left side of the drawing, at the distal tip of the endoscope shaft 92 is cover glass 211, which in this version faces directly along the longitudinal axis of the shaft 92, but may also be positioned at an angle relative to the longitudinal axis as is known in the art. Behind the cover glass 211 is shown a preferred position for the lens 204, set against or very near cover glass 211 and preferably assembled together with the cover glass in construction. While a wide angle lens is shown, this is not limiting and any suitable lens may be used in various embodiments. Further, the particular number and arrangement of lenses in the endoscope shaft 92 will vary widely depending on the application. Optically arranged or attached at the proximal side of lens 204 is a second lens or lens group 209 to focus the incoming light to an appropriate size for the imaging process. The directed light then passes along endoscope shaft 92 and may be guided by other optical elements such as rod lenses. The directed light is received at a doublet lens 210, and directed toward first optical device 208, where it passes through the proximal window 212 of the endoscope 72 and the distal window 213 of first optical device 208. One or more additional lens groups or rod lenses may be included optically positioned between doublet lens 210 and focusing lens group 214. In versions with a unified device, such windows 212, 213 may not be present. Next in the optical path is a deformable lens 202, which is deformable to adjust the optical channel focal length. The deformable lens 202 can be made of, for example, birefringent liquid crystal, a transparent elastic membrane filled with fluid, or a two fluid interface. Preferably such a liquid-based deformable lens is employed, but other suitable deformable lens technologies, as are known in the art, may be used. Depicted are two different deformable surface configurations for the deformable lens. In the first white light imaging mode, deformable lens 202 is configured with the deformable surface at position 215, which generally has more negative lens power than the second fluoresced light configuration position 216 of the deformable lens surface. The deformable lenses can be tuned at least in part by a suitable adjustment mechanism (not shown) such as an electrostatic actuator, an electromagnetic actuator, a piezo-motor, a magneto-strictive actuator, a stepper motor, or an electroactive polymer actuator for a high focus tuning range, or by other methods known in the art. As depicted, the white light configuration position 215 is a negative power lens and the fluoresced light confirmation position 216 is a positive power lens, however this is not limiting, and they may both be negative or both may be positive depending on the optical channel design. Typically, because the chromatic focal difference between the white light image and the fluoresced light image causes a shorter focal distance for the white light, the white light mode will have a comparatively negative lens power than the fluoresced light mode. The deformable lens 202 with its adjustment mechanism is arranged in the first optical device 208 to automatically adjust the focus of the first optical device where the automatic focus adjustment compensates for a chromatic focal difference between the white light image and the fluoresced light image caused by the dispersive or diffractive properties of the optical materials or optical design employed in the assembly construction of the first or second optical devices, or both. The changing of modes, generally automatically performed by the system, in order to provide a real-time overlay, triggers an autofocus algorithm that controls the adjustment of the deformable lens 202. A priori knowledge of the wavelength ranges to be collected in a single frame, for example by identifying characteristics of the light source employed by the medical imaging device, can alert the endoscopic system to the necessary adjustment to the deformable lens 202 for each wavelength range to be detected. Preset positions may be employed for a plurality of modes to achieve the desired configuration, avoiding the need for autofocus processing to determine the desired focal length for each mode. It should also be noted that the inventive system presented herein is not limited to operating between only two modes, but may extend to many wavelength ranges, including small, finite wavelength bands, generally of approximately 10 nm bandwidth, often employed in hyperspectral imaging techniques. As is known in the art, hyperspectral imaging divides the spectrum into many individual bands (as opposed to the three general bands perceived by the human eye), and can extend beyond the visible range into the infrared and ultraviolet ranges, with the goal of attaining a spectrum distribution of light received by each pixel in a sensor array, and combining these intensity/spectra maps into a "hyperspectral cube," generally with the purpose of identifying materials or processes present in the captured subject scene. The present invention does not concern itself with applications or analysis of the collected hyperspectral cube, but rather enables the collection thereof in a manner not previously possible.

Next in the optical path is a focusing lens group 214 which in this version includes a plano-convex lens and a doublet lens including a biconvex lens and a biconcave lens. Many other suitable lenses and combinations of lenses may be used. Focusing lens group 214 focuses the image light toward the image sensor 222 which may include a cover glass.

In one example embodiment image sensor 222 is a single sensor capable of detecting both visible light images and fluoresced light images, for example visible light imagery at approximately 450-650 nm wavelength, and the infrared fluorescence imagery at 800-900 nm. Additionally, or alternatively, the sensor may detect other fluorescent wavelengths commonly used in endoscopic imagery in addition to the visible light wavelengths. Because the fluorescent imagery is focused in a different plane than the visible light, the device has the capability of adjusting the optical path focus when switching between visible light mode and FI mode as described above.

It should be noted that while the position of the deformable lens 202 is shown before the focusing lens group 214 in this embodiment, this is not limiting, and the deformable lens 202 may be placed in any suitable location in the optical channel where the channel construction can accommodate the varied focal lengths resulting from changing the deformable lens configuration. For example, deformable lens 202 may be part of the focusing lens group 214.

Figure 3:
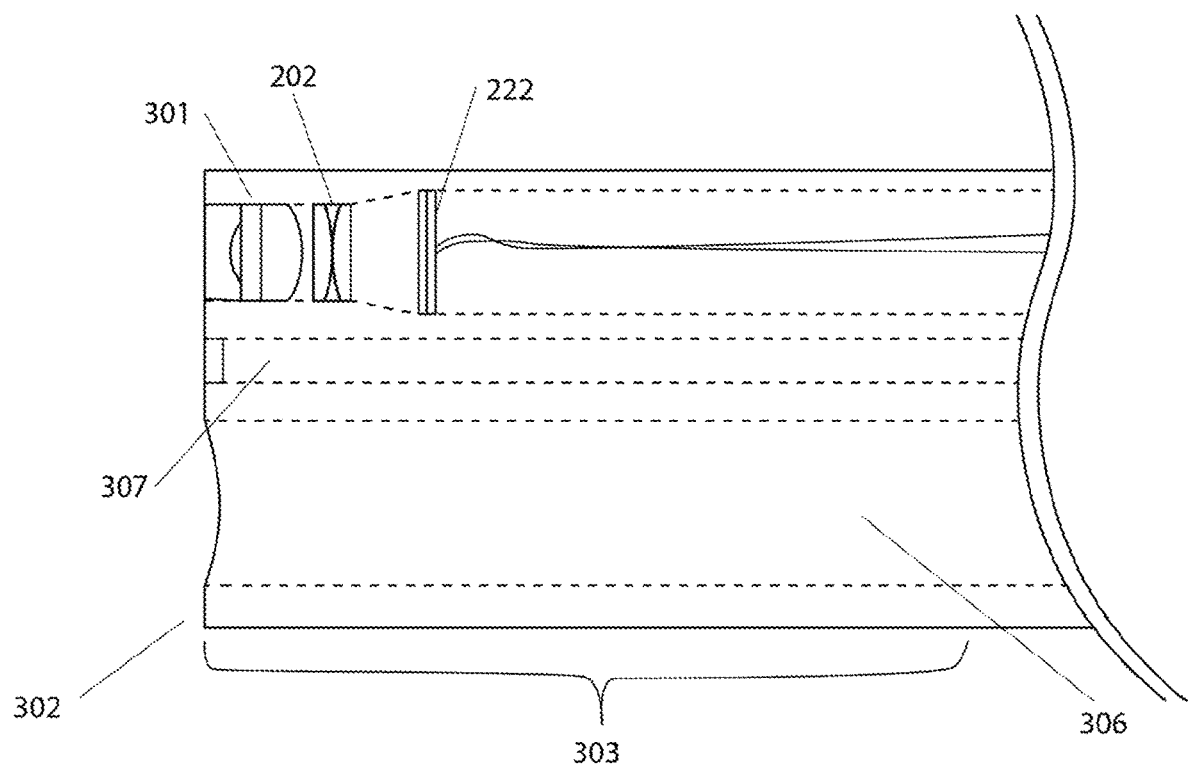
FIG. 3 illustrates a cross section of an embodiment of the invention employing a distal tip imaging system.

While the embodiment described above with relation to FIG. 2, offers many advantages over the current state-of-the-art endoscopic systems already discussed, for example, offering the ability to correct chromatic longitudinal aberration across various spectrum ranges for pre-existing endoscopes to be attached thereto, it should also be noted that the present invention is not limited to embodiments wherein the deformable lens is located in a camera head removably attached to an endoscope. FIG. 3, for example, shows an embodiment of the invention wherein the deformable lens is present in in the distal tip of a video endoscope. Such distal tip video endoscopes (COTT) can be rigid or flexible scopes. FIG. 3, while not limiting, exhibits the optical system in an exemplar flexible endoscope. Many of the optical elements corresponding to those in FIG. 2 are not repeated here. A first optical group 301, located at the distal end 302 of the distal tip 303 of the endoscope, comprises a cover glass and objective lens. In many embodiments the cover glass is an element of the objective lens and first optical group 301. Downstream from the first optical group is the deformable, variable focus lens 202, that, in a similar manner to that shown in FIG. 2, is employed to adjust the focal length corresponding to the viewed wavelength range, in order to provide an in-focus image falling on the image sensor 222. The distal tip, flexible endoscopic system may also employ a working channel 306 through which tools may be introduced to the surgical site, and through which material may be removed therefrom. In addition, one or more light guides 307 may be present in order to provide illumination at the desired wavelength ranges to the subject scene. The light guides may be attached by and comprise optical fibers connected to a light source (80 of FIG. 1), as known in the art. Alternately, distally placed LEDs may be present to provide illumination. Of course, though not explicitly shown in the other figures, including FIG. 2, other embodiments, including rigid systems, such as those described in the remaining figures, often also include light guides and working channels.

Figure 4:
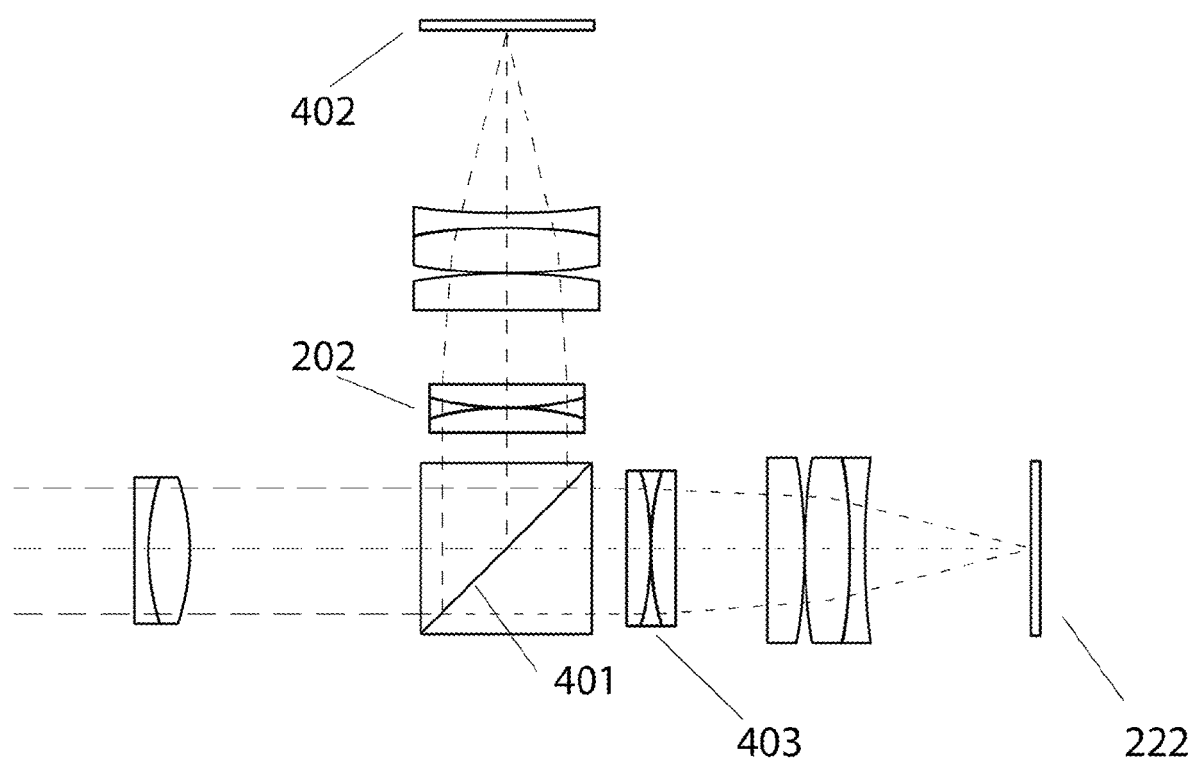
FIG. 4 is a schematic representation of another embodiment of the invention wherein incoming light is split into two beams and at least one resulting optical channel employs a deformable lens.

A schematic depiction of the optical system of another embodiment is shown in FIG. 4, that may be combined with others described in this disclosure, enables the selection of particular wavelength ranges, through the inclusion of tunable spectral filters along the optical path of one or more beams.

The depicted system uses a dichroic beam splitter 401 to direct a first beam of light for example, the visible image light, to a first image sensor 222 and a second beam of light, for example the fluoresced light to a second image sensor 402. In this example, fluoresced light enters and is reflected upwards by a dichroic prism interface of beam splitter 401 and is incident upon the fluorescence image sensor 402, while the visible light is passed through the interface 401 to image sensor 222. Beam splitter 401 is preferably a dichroic prism or other suitable dichroic optical element, having a low-pass reflective surface at a 45 degree angle allowing higher frequencies to pass through to visible light image sensor 222 and lower frequencies to reflect to fluorescence sensor 402. The cutoff frequency may be positioned at or near the top wavelength of visible light, that is near 650 nm, or higher as long as it is below the lowest frequency (higher than longest wavelength) required for detection of the fluoresced light. While the beam splitter 401 in this version transmits the visible light wavelengths and reflects the fluoresced light wavelengths, this is not limiting and other versions may pass the fluorescence light and reflect the visible light (with a high-pass dichroic prism, for example), or may reflect both in differing directions.

Image sensor 222 is cable of detecting the visible light wavelengths commonly used for endoscopic examination, for example visible light imagery at approximately the 450-650 nm wavelengths. In this version, image sensor 402 is a single sensor capable of detecting fluoresced light images, infrared fluorescence imagery, for example, at 800-900 nm. Additionally or alternatively, the sensor may detect other fluorescent wavelengths commonly used in endoscopic imagery.

As shown, the fluorescence imaging optical path between the beam splitter 401 and fluorescence image sensor 402 also comprises a deformable, variable-focus lens 202 in order to adjust the focal plane for the fluoresced light based on characteristics of the attached endoscope, such as the aberration characteristics or the use of a differing fluoresced wavelengths in differing scopes for use with various fluoresced imaging techniques or to correct for longitudinal chromatic aberration in a distal tip endoscope. The adjustment mechanism for variable lens 202 may any of those known in the art. The required focal length adjustment provided by the variable focus lens 202 in this embodiment will typically be less than that required to adjust for differing focal lengths between visible and fluoresced light, as this embodiments adjusts only for different fluoresced light characteristics of the optical channel such as dispersion and chromatic focal differences, or for differences in focal length relating to various FI imaging techniques, all taking place within the wavelength region longer that of the visible spectrum. This embodiment allows, thereby, the dedication of one sensor to the collection of fluorescence images, allowing more light to be captured by, for example, the use of a monochromatic sensor for the fluorescence image sensor 402, obviating the need for a Bayer filter on this sensor. This two chip design permits, as do previously explained embodiments, sequential imaging, and thus near real-time video with the FI image overlaid with the visible light image, as will be further discussed below. Alternatively, of course, the images can be displayed separately or as a "picture-in-picture" image on a single display (FIG. 1, 76). This embodiment uses deformable lens 202 primarily to adapt to optics already present in the attached endoscope improving compatibility with an FI technique used, enabling thereby in-focus overlays of both FI and visible light irrespective of the optical properties of the attached endoscope (or permanent optics) and the FI technique being used by a simple calibration, autofocus algorithm, and/or a computation based on a priori knowledge of the associated optics and FI spectrum range. Optionally, a second deformable, variable-focus 403 may be placed in the optical channel between the beam splitter 401 and the first image sensor 222.

Figure 5:
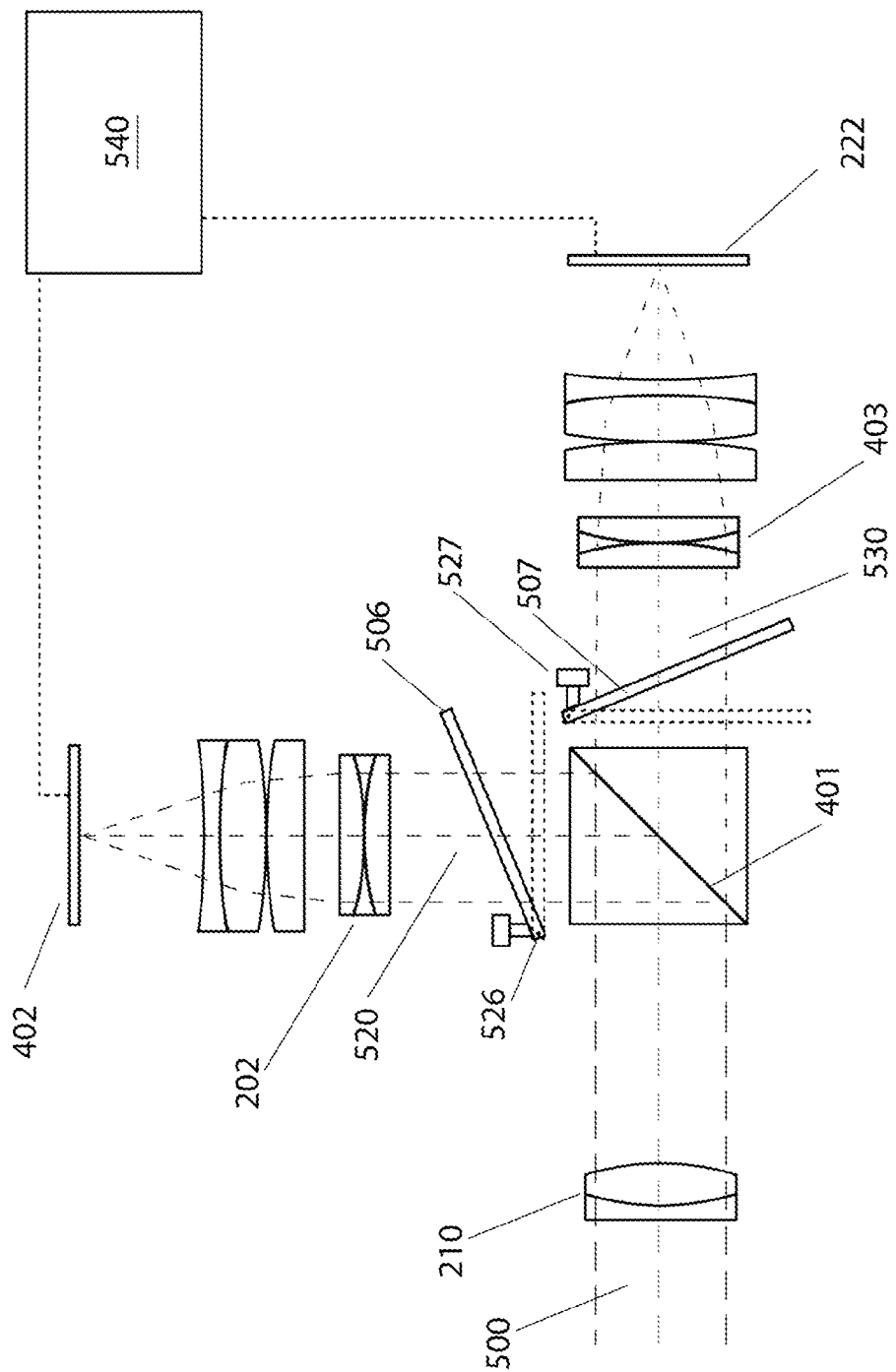
FIG. 5 illustrates an embodiment of the invention similar to that shown in FIG. 4 further comprising one or more variable wavelength band filter elements.

A further implementation of the present invention is shown in relation to the embodiment of FIG. 5. This embodiment, and variations thereof, utilize variable optical spectrum filters, as discussed in detail in co-pending German Patent Application 102019134314.3. As in the version shown in FIG. 4, the endoscopic system comprises image collecting and (optionally) image relaying optics 210 such as an objective, an eyepiece, a lens, a prism, an optical waveguide or the like, located upstream of at least one beam splitter 401. Viewed in the direction of incidence of the input beam path 500, the beam splitter 401 is arranged downstream from the image collecting and relaying optics 510. The beam splitter 401 splits the input beam 500 into at least two beams 520, 530. The beam splitter 401 may split the input beam 500 into essentially equal parts, or non-equal parts, depending on the desired application. The endoscopic system utilizes at least two image sensors 222, 402. Each image sensor 222, 402 is designed to capture image information at a frame rate of at least 10 frames per second. Preferably, the image sensors are designed to capture at least 30 images per second. The image sensors in the present case may be CMOS sensors, although other sensors known in the art, such as CCD sensors may also be employed. In addition, the image sensors 222, 402, should not be limited to consisting of only a single sensor array for each sensor, but each image sensor may comprise multiple sensor arrays, the data from which may be combined, as appropriate, into a single image by an image processor 540.

The endoscopic system of this embodiment comprises at least one optical filter unit 506 placed within the optical path 520 between the image beam splitter 401 and one of the image sensors 402. The optical filter unit 506 comprises at least one spectral filter. While the optical filter may comprise more elements than the spectral filter, we will use the terms interchangeably in order to improve simplicity of disclosure, with the understanding that the optical filter 506 includes at least a spectral filter. In general, the spectral filter is a band pass filter. In the illustrated case, the spectral filter is separate from the beam splitter 401. However, in some embodiments the beam splitter 401 can form at least an element of the spectral filter, whereby components and/or installation space could be reduced advantageously, as an additional spectral filter could be dispensed with. The spectral filter 506 has at least two angular positions along the optical path 520 relative to the image sensor 402. The spectral filter 506 can be toggled between the two or more angular positions. Further angular positions, in particular intermediate positions, of the spectral filter 506 relative to the image sensor 402 are also possible in various embodiments of the invention. Each differing angular position results in the transmission of different wavelength ranges of light to the image sensor 402. In addition, the spectral filter 506 may be continuously adjustable relative to the image acquisition sensor 402. In general, the angular position of the spectral filter 506 is tilted to change from the first position to the second position. The spectral filter 506 can be tilted about a swivel axis 516, which is generally parallel to the plane in which the filter lies (depicted in this example as orthogonal to the plane of the paper in FIG. 5). As shown in FIG. 5, the swivel axis 516 is defined from a side edge of the spectral filter 506, however this should not be considered limiting as it is possible that the spectral filter 506 may be rotatable/tiltable, in particular around a yaw, vertical and/or vertical axis of the spectral filter 506.

The first angular position and the second angular positions of the spectral filter 506 differ in the orientation image sensor 402. The change in angle of deviation from the first position to the second position is generally at least 2°. This angle will also be not more than 45°. As illustrated in FIG. 5, the angle is essentially 25° (original sensor position indicated by dotted lines).

The optical filter 506 may have at least one support mechanism (not shown) such as a swivel bearing, designed to support the spectral filter 506 from the first position to the second position and/or vice versa. The bearing could also be a tilting and/or pivot bearing. The optical filter unit 506 has at least one actuator 526. The actuator 526 is designed to transfer the spectral filter 506 from the first position to the second position and/or vice versa. The actuator 526 is also designed to transfer the spectral filter 506 from the second position to the first position and back to the second position at least 10 times per second. Accordingly, the spectral filter 506 is capable of changing its position at least 20 times per second, however, ideally, changes on the order of 30 times or more per second are desired in order to produce video signals standard to the industry. The actuator 526 may be, for example, a stepper motor. Steps of the actuator 526 correspond with angular segments of the angle between the first position and the second position of the spectral filter 506 relative to the optical path 520 between the beam splitter 401 and the image sensor 402.

The pivoting spectral filter 506 in the first position has a first transmission range of wavelengths (wavelength band) which it passes there through to the image sensor 402. The second position has a second transmission range of wavelengths which it passes there through to the image sensor 402. Therefore, by altering the angular position of the spectral filter 506, as described above, various spectral bands can be detected by the image sensor 402, while others are rejected, not being passed through the filter. Thus, the second spectral transmission range is at least partially different from the first spectral transmission range, and in this way the spectral bands observed by image sensor 402 can be selected by the adjustment of the angle of the pivotable spectral filter 506 relative to the optical path 520 between the image sensor 402 and the beam splitter 401.

In order to assure that the image collected at this spectrum is properly in-focus, variable-focus, deformable lens 202 is positioned, generally, between the spectral filter 506 and the image sensor 402. Additional non-varying, focusing and/or directing optics may also be present as seen in the figure. The deformable lens 202, is programmed to adjust the focal plane based on the known value of the band of the spectrum passing through the spectral filter 506 at a given instant. Therefore, by coordinating the angular position of the filter 506 and the focal length of the deformable lens 202, it is possible to ensure an in-focus image is received for each frame captured by the image sensor 402. For an ensuing frame, the position of the sensor 506 may be changed to the second position, and the focal length of the deformable lens 202 is correspondingly changed in order that the image sensor 402 captures a second in-focus image at the second transmitted spectral band. Of course, the present invention is not limited to two modes of operation, but enables the collection of as many, distinct, in-focus spectral bands as may be adequately filtered with a variable position filter as described above. In this matter the invention enables hyperspectral imaging by collecting images produced in narrow wavelength bands of a single scene, and offers the added benefit of the ability to ensure that each wavelength band is collected in the proper focus due to the synchronized deformable lens. Further discussion regarding synchronization will be presented below. In one embodiment of the illustration also shown in FIG. 5, the second optical channel 530, between the beam splitter 401 and a second image sensor 222 may or may not contain a spectral filter unit 507 and/or a deformable lens 40. Embodiments not containing these elements may contain corresponding non-variable elements, or, may contain one, but not the other element. For example, in a system where the beam splitter 401 passes wavelengths in the visible spectrum, from about 380 nm to 740 nm, to the second image sensor 222, and reflects other wavelengths in the direction of the first image sensor 402, it may still be advantageous to employ an additional fixed wavelength filter in order to filter out undesired wavelengths, or it may be advantageous to include a deformable lens 403 in this optical channel 530 in order to correct any focal plane issues caused by the optics of a particular attached endoscope. Alternatively. a fixed focal length lens may adequate along this channel, and reduce the complexity and cost of the overall system over one employing one with a deformable lens along this channel. Such an embodiment could be ideal for applications such as FI/visible light video overlays.

While the embodiments represented by FIG. 5 discussed above require only one variable spectral filter and one deformable lens, further versatility and other advantages are enabled by employing a second variable spectral filter 507 (and associated actuator 527) and second deformable lens 403 in the second optical channel 530. In particular, this variation offers advantages with regard to hyperspectral imaging. In this case, one sensor can be dedicated to a first range of wavelengths, while the other sensor is dedicated to a separate, distinct range, and each optical channel can employ elements, such as specific dichroic filters, particularly chosen to optimize their use in a particular application. For example, the first spectral filter 506 might have an operable variability range between 1000-2000 nm and the second spectral filter 507 might have an operable variability range between 400-1000 nm, and the beamsplitter 401 may be chosen such that wavelengths over 1000 nm are directed toward the first image sensor 402 and wavelengths under 1000 nm are directed toward the second image sensor 222. Images from each detector may be captured rapidly and sequentially, changing the selected wavelength range passed by each of the two filters 506, 507, and adjusting each of the deformable lenses 202, 403 between each collected frame, and the resulting image data can be transmitted to an image processor 540 to generate hyperspectral data, such as a hyperspectral cube, containing the data for each wavelength band. It should further be noted that in addition to the adjustments in the optical system between each collected frame described above, the integration time of the image sensor, or the illumination intensity may also be varied, as necessary, to obtain an image of desired exposure, with the understanding that some wavelength bands may, for the same integration time, yield images of lesser intensity, and therefore longer integration times are desired.

Another variation of the invention employs one or more image sensors 402, 222 wherein a portion of the individual pixels are filtered by means of filter elements associated with individual or groups of pixels. By way of example, the Bayer filter, well known in the art and used in many color image sensors, filters pixels in sets of four: two green pixels, one red pixel and one blue pixel, and the resultant data is used to generate a color image. In contrast, the present invention could use, for example, an image sensor where every other pixel is filtered between 1000-2000 nm or between 400-1000 nm, allowing, thereby, the ability to double the frame rate achievable, by collecting data at these two ranges simultaneously, and utilizing an image processor to generate a hyper spectral image; in this way a single acquisition cycle can collect an image in two spectral ranges. Of course, such a filtered image will trade off captured image resolution for the multiple filtered images, just as a Bayer filter sacrifices resolution for the ability to generate color images. These specialized filters can be used in any of the embodiments presented herein when corresponding image processing is applied.

Figure 6:
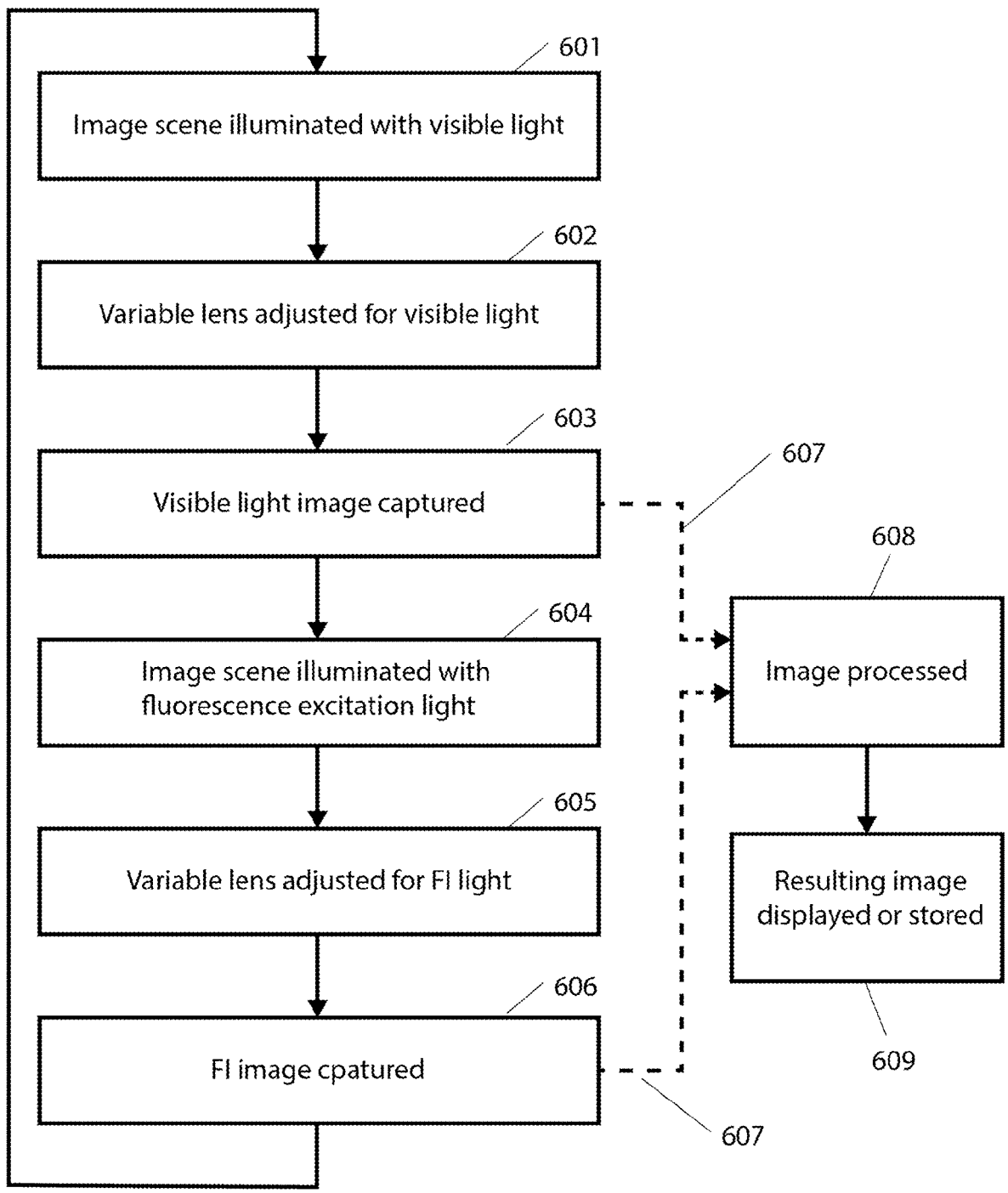
FIG. 6. is a representation of a timeline for image acquisition for some embodiments of the invention with a single optical channel.

Synchronization and timing are of the various components of the disclosed embodiments are an important part of the present invention. For fluorescent imaging, a light source 80, such as that shown in FIG. 1, must provide illumination to the subject scene at a wavelength or range of wavelengths that result in targeted tissue fluorescing. In the case of the commonly used ICG FI techniques, excitation radiation in the near infrared (NIR) spectrum, generally between 600-900 nm, is required, and results in emission radiation with maximum intensity in the range of about 830 nm. By contrast, illumination over a wide range from 380-740 nm is desirable for visible light imaging. Accordingly, the present example implementation synchronizes the light source with the other elements disclosed above. FIG. 6 illustrates a timeline for acquisition and presentation of video data for an embodiment of the present invention such as those illustrated in FIG. 2 or FIG. 3, wherein a single optical channel is generally present. At an initial time 601 the subject scene is illuminated with visible light, simultaneously, before or after the start of this illumination period, the visible light channel deformable lens is adjusted 602 such that an in-focus image is captured 603 by the image sensor. It should be noted, that while the adjustment to the deformable lens may take place before or after the initial illumination of the images scene with visible light, it must be maintained in this configuration for the duration of the capture of the visible light image. The captured image is subsequently transmitted 607 to an image processor. Subsequent to the capture 603 of the visible light image, the subject scene is illuminated with excitation radiation 604 in order to generate fluorescence of the ICG present in the scene. Before, after or during the change in radiation to excitation illumination 604, but after the capture of the visible light image 603, the deformable lens is adjusted 605 such that an in-focus FI image is captured 606. Again, it should be noted, that while the adjustment to the deformable lens may take place before, after or during the initial illumination of the subject scene with excitation light, it must be maintained in this configuration for the duration of the capture of the FI image 606. Subsequently the captured in-focus FI image is transmitted 607 to the image processor. The image processor may then combine or otherwise process the images 608 by means known in the art, and store or output the images to a video display 609. Alternatively the images may be presented on video display as a picture-in picture or side-by side, or other presentation known in the art. Subsequent to the acquisition of the FI image, the cycle, may return to step 601 to capture another frame. The processed images may be presented on a video display at a rate limited only by the time required to perform these steps, preferably at a rate of at least 10 fps, though, more preferably at a rate of 30 fps.

In a process similar to that shown in FIG. 6, a system employing a single optical channel can also be used to perform hyperspectral imaging. In this case the scene could be illuminated by a narrow wavelength band, such as illumination produced by a light emitting diode, with a bandwidth of, for example, 20 nm. The deformable lens 202, is then adjusted such that an in-focus image is detected and captured by the image sensor 222. The light source 80 is then adjusted such that the scene is illuminated in an adjacent wavelength band, the deformable lens 202 is adjusted such that a second in-focus image is detected and captured by the image sensor 222. This process continues over the desired wavelength ranges, to produce, in the end, a hyperspectral cube, as known in the art, capable of later analysis and/or display.

Figure 7:
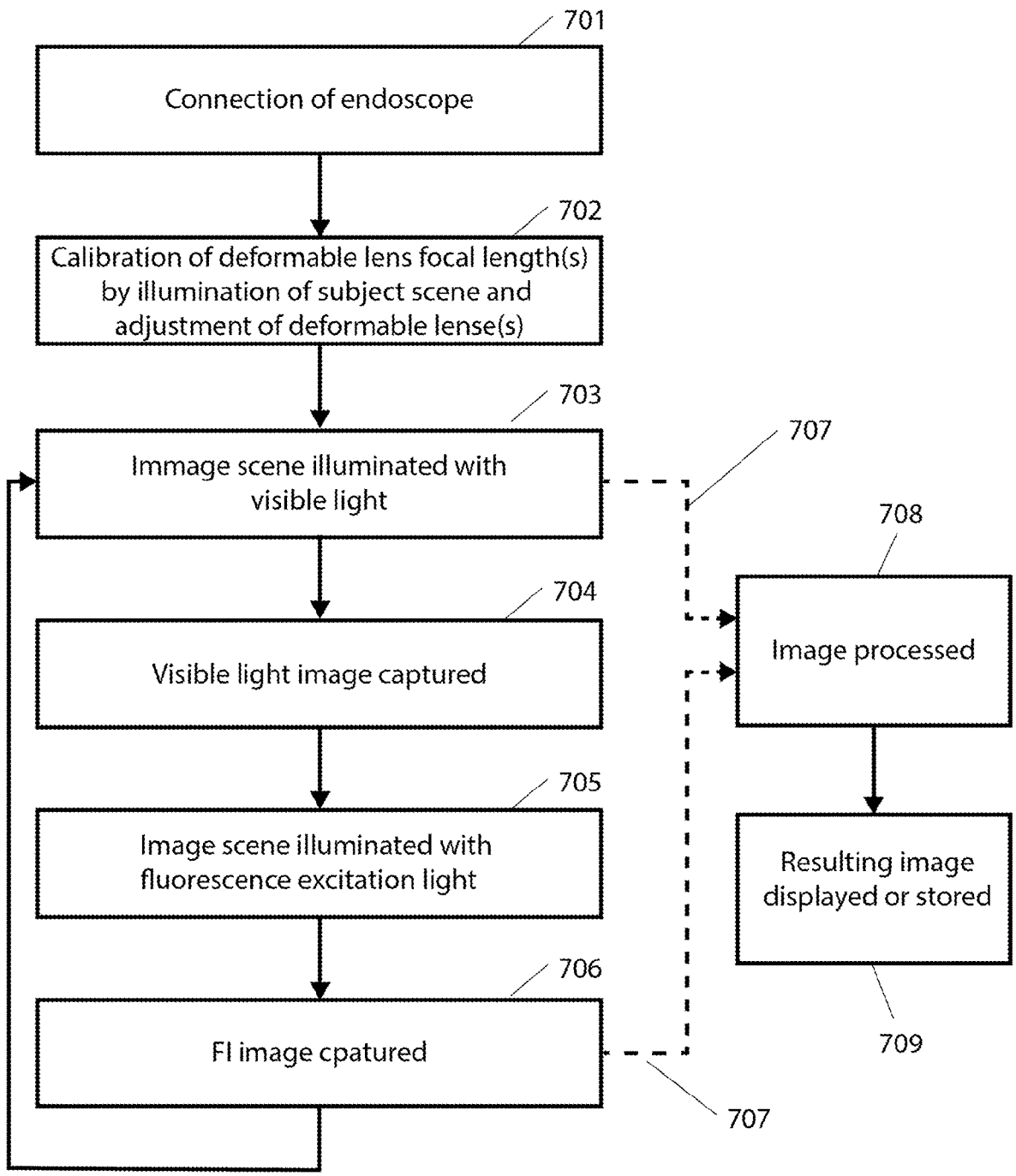
FIG. 7 is a representation of a timeline for image acquisition for some embodiments of the invention with more than one optical channel and including a calibration step for the variable focus optics.

FIG. 7 shows an inventive synchronization timeline method according to the dual optical channel medical imaging device embodiment shown in FIG. 4. In this process, an endoscope, or other image collecting optics (for example, in the case of a combined endoscope/image acquisition system, this step might be performed as a final calibration step in the instrument manufacture procedure), is connected 701 to an image acquisition system such as a camera head. In order to calibrate the system, the scene is illuminated with excitation light and deformable lens 202 is adjusted 702 such that an in-focus image is captured at the FI image sensor 402. Optionally, when a deformable lens 403 is also included in the second optical channel, a similar calibration procedure 701,702 can be performed, if necessary, to ensure an in-focus visible light image at the associated image sensor 222. Subsequent to this calibration step, at a first acquisition time, the scene is illuminated with white light 703 and a visible spectrum image is captured 704 at the first image sensor 222. The captured visible spectrum image is transmitted 707 to an image processor 540. At a second acquisition time, the scene is illuminated with excitation light 705 and an FI image is captured 706 at the second image sensor 402. The captured FI image is transmitted 707 to the image processor 540. It is important to note that the first acquisition time may occur subsequent to the second acquisition time, with the limitation being that the two acquisition times cannot overlap in time, and that when the visible spectrum image is captured, the scene must be illuminated with white light and when the FI image is captured, the scene must be illuminated with fluorescence inducing excitation light, and, optimally, the scene should not be illuminated by excitation light and visible light simultaneously, as the intensity of the image produced by the visible illumination generally drowns out any FI image received due to the overlap of the illumination spectra. The FI image is captured 706 and transmitted 707 to an image processor 540. The image processor may then combine or otherwise process 708 the images, by means known in the art, and store, or output the images to a video display 709. Alternatively the images may be presented on video display 76 as a picture-in picture or side-by side, or other presentation scheme known in the art. Subsequent to the acquisition of the FI image 706, the cycle, may return to step 703 to capture another frame. The processed images may be presented on a video display 76 at a rate limited only by the time required to perform these steps, preferably at a rate of at least 10 fps, though, more preferably at a rate of 30 fps.

With respect to FIGS. 6 and 7, it should be noted that the terms visible light and excitation light are used as examples only, and should not be considered limiting. Of course, other wavelength ranges could be substituted in either case as appropriate, for example FI imaging could be replaced with a UV analysis, and visible light imaging could be replaced by a narrow bandwidth color illumination, rather than white light.

Figure 8:
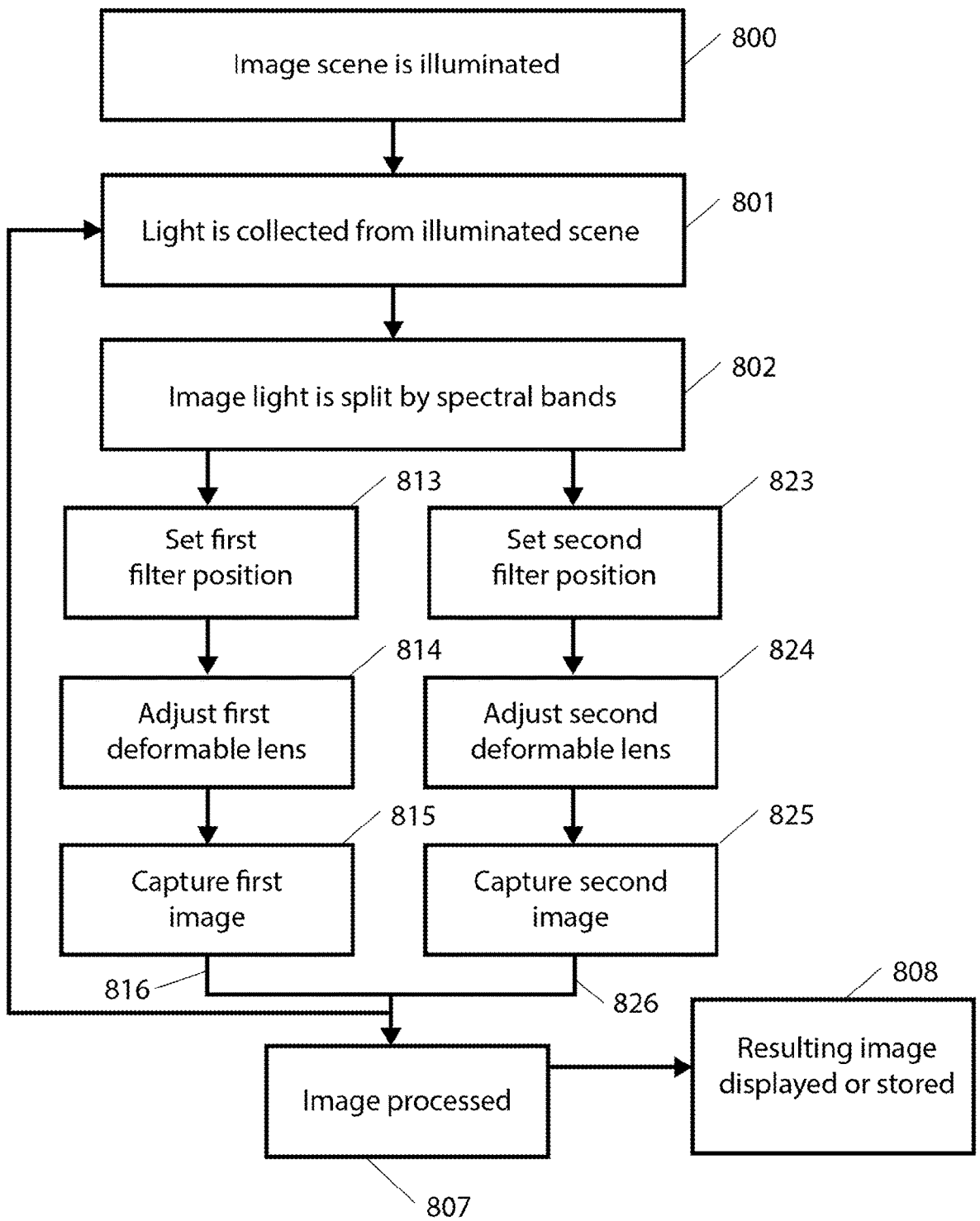
FIG. 8 is a representation of a timeline for image acquisition for some embodiments of the invention involving multiple optical channels and variable spectral filtration.

FIG. 8 represents a timeline for an example hyperspectral imaging process with reference to the embodiment shown in FIG. 5, in which narrow bands of illumination are imaged on sensors 402 and 222 and a composite hyperspectral cube is formed from the collected data. In this example, the sample scene is illuminated 800 with a broad spectrum of radiation, for example light with a spectrum from 400 nm to 1000 nm. The light is collected 801 by appropriate optics, such as the objective on an endoscope, and transferred to a beam splitter 401 that, in this example, splits 802 the beam by wavelength bands, with light of a wavelength greater than 1000 nm proceeding along a first optical path 520 and light with a wavelength less than 1000 nm proceeding along a second optical path 530. Along the first optical path, an appropriate angle of the first variable spectral filter 506 is selected and positioned 813 to permit the passage of only a specific spectral band to the first image sensor 402. The first variable focus lens 202 is adjusted 814 such that an in-focus image is received at the first image sensor 222. It should be noted that steps 813 and 814 can happen sequentially, simultaneously, or in reverse order. An image of the scene at a first wavelength range is captured 815 at the first image sensor 222 and transmitted 816 to an image processor 540. It should be noted that step 815 may also include varying the integration time of the image sensor 222, as appropriate, to acquire an image of sufficient exposure to be useful in as an element of the hyperspectral cube. Simultaneously to steps 813, 814 and 815, or previously, or subsequently, along the second optical path 530, an appropriate angle of the second variable spectral filter 507 is selected and positioned 823 to permit the passage of only a narrow spectral band to the second image sensor 222. The second variable focus lens 403 is adjusted 824 such that an in-focus image is received at the second image sensor 222. It should be noted that steps 823 and 824 can happen sequentially, simultaneously, or in reverse order. An image of the scene at a second wavelength range is captured 825 at the second image sensor 222 and transmitted 826 to an image processor 540. It should be noted that step 825 may also include varying the integration time of the second image sensor, as appropriate, to acquire an image of sufficient exposure to be useful in as an element of the hyperspectral image data, including the generation of a hyperspectral cube. The image processor 540 may then process the images 807 or store, display, and/or transmit them 808. Subsequent to transmission steps 816, 826, the process may return to step 801 for the collection of subsequent frames of the subject scene, to, generally, be collected at other narrow wavelength bands by subsequent adjustment of the filter 506, 507 positions and corresponding adjustment of the variable focus lenses 202, 403.

It should also be noted that the process shown in FIG. 8 may also comprise the step, as an element of Step 800, of illuminating the subject scene with a narrow band of illumination, rather than a broad spectrum. In this case, techniques known in the art, such as narrow band LED illumination, may be used to illuminate the scene. Further, after transmittal of signals 816, 826 to the image processor, the cycle may return to step 800, rather than 801, wherein the illuminating wavelength bands are changed by, for example illumination with a new narrow wavelength source, such as a narrow band LED source.

Figure 9:
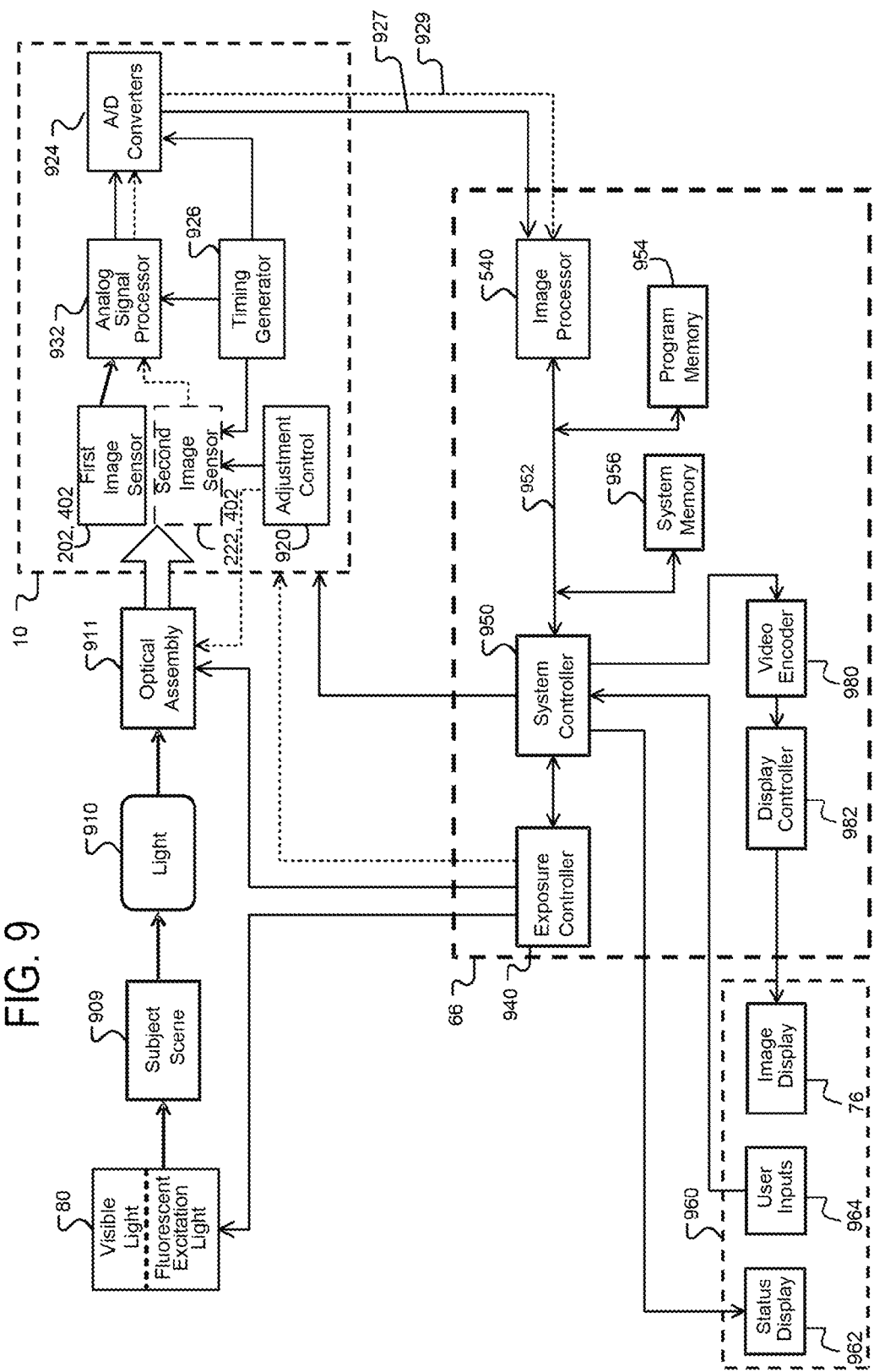
FIG. 9 is a block diagram representing hardware of a system according to some implementations of the invention.

Referring to FIG. 9, a block diagram of system including an image capture device according to an example embodiment of the invention is shown. The invention is applicable to more than one type of device enabled for image capture, such as endoscopes incorporating solid state imagers, digital microscopes, digital cameras, mobile phones equipped with imaging sub-systems. The preferred version is an imaging scope system, such as an endoscope.

A light source 80 illuminates subject scene 909 with visible light and/or fluorescent excitation light, which may be outside the visible spectrum in the ultra-violet range or the infra-red/near infrared range, or both. Light source 80 may include a single light emitting element configured to provide light throughout the desired spectrum, or a visible light emitting element and a one or more fluorescent excitation light emitting elements. Further, light source 80 may include fiber optics passing through the body of the scope, or other light emitting arrangements such as LEDs or laser diodes positioned at or near the front of the scope.

As shown in the drawing, light 910 scattered or reflected from (or, alternatively, as in the case of fluorescence, emitted by) the subject scene 909 is gathered by an optical assembly 911, where the light is focused to form an image at a solid-state image sensor(s) and/or fluoresced light sensor(s) 222, 402.

Optical assembly 911 includes at least one lens 204, which may be a wide-angle lens element such that optical assembly 911 directs and focuses light which generally represents a wide field of view. The deformable lens 202 (or lenses 202, 403) is (are) part of the optical assembly. As discussed above, portions of the optical assembly may be embodied in a camera head or other first optical device 208, while other portions are in an endoscope 72 or other scope device, or the optical assembly 911 may contained in a single imaging device. Image sensor 222, 402 (which may include separate R, G, and B sensor arrays) and fluoresced light sensor 222, 402 convert the incident visible and invisible light to an electrical signal by integrating charge for each picture element (pixel). It is noted that fluoresced light sensor 222, 402 is shown as an optional dotted box because embodiments may use a single sensor 222 to detect both visible light and fluoresced light. The latter scheme may be used when the fluoresced light is in a spectrum detectable by image sensor 222 that is in or near the visible light spectrum typically detected by a RGB sensor arrays.

The image sensors 222, 402 may be active pixel complementary metal oxide semiconductor sensor (CMOS APS) or a charge-coupled device (CCD).

The total amount of light 910 reaching the image sensor(s) 222, 402 is regulated by the light source 80 intensity, the optical assembly 911 aperture, and the time for which the image sensors 222, 402 integrate charge. An exposure controller 940 responds to the amount of light available in the scene given the intensity and spatial distribution of digitized signals corresponding to the intensity and spatial distribution of the light focused on image sensor(s) 222, 402.

Exposure controller 940 also controls the emission of fluorescent excitation light from light source 80, and may control the visible and fluorescent light emitting elements to be on at the same time, or to alternate to allow fluoresced light frames to be captured in the absence of visible light if such is required by the fluorescent imaging scheme employed. Exposure controller 940 may also control the optical assembly 911 aperture, and indirectly, the time for which the image sensor(s) 222, 402 integrate charge. The control connection from exposure controller 940 to timing generator 926 is shown as a dotted line because the control is typically indirect.

Typically, exposure controller 940 has a different timing and exposure scheme for each of sensors 222, 402. Due to the different types of sensed data, the exposure controller 940 may control the integration time of the sensors 222, 402 by integrating a visible light sensor 222, 402 up to the maximum allowed within a fixed 60 Hz or 50 Hz frame rate (standard frame rates for USA versus European video, respectively), while a fluoresced light sensor 222, 402 may be controlled to vary its integration time from a small fraction of visible light sensor frame time to many multiples of visible light sensor 922. The frame rate of visible light sensor will typically govern the synchronization process such that image frames based on the visible light sensor 923 are repeated or interpolated to synchronize in time with the 50 or 60 fps rate of a fluorescence sensor. Alternately, the frame rate of the visible light sensor may be slowed to match that of a fluorescence sensor.

Analog signals from the image sensor(s) 222, 402 are processed by analog signal processor 932 and applied to analog-to-digital (A/D) converter 924 for digitizing the analog sensor signals. The digitized signals each representing streams of images or image representations based on the data, are fed to image processor 540 as image signals 927, 929. For versions in which a single image sensor 222 also functions to detect multiple wavelength bands both streams of data are included in the image signal 927, typically in one or more of three color channels.

An adjustment control circuit 920 may be provided for supplying the driving signals to operate the adjustment mechanism for the deformable lenses 202, 403 and variable spectral filters 506, 507 according to the various embodiments herein. For versions in which image filter positions are adjusted, the adjustment control circuit sends appropriate driving signals to the mechanical or electrical actuators 526, 527, such as a piezo-electric motor, and may also receive position signals back from the actuators. Adjustment control circuitry 920 sends appropriate drive signals to the deformable lens 202, 403 adjustment mechanism, such as an actuator or piezo-electric motor, and may also receive position signals from the adjustment mechanism. Image processor 540 includes circuitry performing digital image processing functions to process and filter the received images as is known in the art. Image processor may include separate, parallel pipelines for processing the visible light image data and FI image data separately. Such circuitry is known in the art and will not be further described here. In some embodiments, image processor 540 may also perform known autofocus algorithms to allow feedback control of adjustment control circuitry 920 to compensate for chromatic focal difference between the white light image and the fluoresced light image. However, in preferred embodiments, such adjustments are predetermined and stored in system memory 956 to allow quick and reliable focus adjustment. In some versions, the predetermined settings may be stored in memory in the first optical device 208 itself rather than a camera control unit (CCU) 66 or other attached controller.

Image processor 540 may provide algorithms, known in the art, for combining visible light imagery with FI imagery in a combined image display, and further highlighting or emphasizing the FI imagery for easily distinguishing the presence of fluorescing features in the image, or generation of hyperspectral data or other multiple wavelength band analysis.

Timing generator 926 produces various clocking signals to select rows and pixels and synchronizes the operation of image sensors 222, 402, analog signal processor 932, and A/D converter 924. Imaging unit 10 includes the image sensors 222, 402, adjustment control 920, the analog signal processor 932, the A/D converter 924, and the timing generator 926. The functional elements of the imaging unit 10 can be fabricated as a single integrated circuit as is commonly done with CMOS image sensors or they can be separately-fabricated integrated circuits.

The system controller 950 controls the overall operation of the image capture device based on a software program stored in program memory 954. This memory can also be used to store user setting selections and other data to be preserved when the camera is turned off.

System controller 950 controls the sequence of data capture by directing exposure controller 940 to set the light source 80 intensity, the optical assembly 911 aperture, and controlling various filters in optical assembly 911 and timing that may be necessary to obtain image streams. In some versions, optical assembly 911 includes an optical filter configured to attenuate excitation light and transmit the fluoresced light. A data bus 952 includes a pathway for address, data, and control signals.

Processed image data are continuously sent to video encoder 980 to produce a video signal. This signal is processed by display controller 982 and presented on image display 76. This display is typically a liquid crystal display backlit with light-emitting diodes (LED LCD), although other types of displays are used as well. The processed image data can also be stored in system memory 956 or other internal or external memory device.

The user interface 960, including all or any combination of image display 76, user inputs 964, and status display 962, is controlled by a combination of software programs executed on system controller 950. User inputs typically include some combination of typing keyboards, computer pointing devices, buttons, rocker switches, joysticks, rotary dials, or touch screens. The system controller 950 manages the graphical user interface (GUI) presented on one or more of the displays (e.g. on image display 988). System controller 950 may receive inputs from buttons or other external user interface controls on the scope itself (or software controls through the GUI) to receive inputs to control the process for automatically adjusting the focus according to the present invention. In particular, the system controller 950 will typically have a mode toggle user input (typically through a button on the endoscope or camera head itself, but possibly through a GUI interface), and in response transmit commands to adjust image processing circuitry 930 based on predetermined setting stored in system memory. Such settings may include different settings for different models of scopes that may be attached to a camera head or other imaging device containing imaging unit 10.

Image processor 540 is one of three programmable logic devices, processors, or controllers in this embodiment, in addition to a system controller 950 and the exposure controller 940. Image processor 540, system controller 950, exposure controller 940, system and program memories 956 and 954, video encoder 980 and display controller 982 may be housed within camera control unit (CCU) 66.

CCU 66 may be responsible for powering and controlling light source 80, imaging unit 928, and/or optical assembly 911. In some versions, a separate front end camera module may perform some of the image processing functions of the image processor 540.

Although this distribution of imaging device functional control among multiple programmable logic devices, processors, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions, and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. A method for generating hyperspectral image data by collecting image light with a medical imaging device, the hyperspectral image data comprising a plurality of individual video frames, each video frame comprising an image collected at a distinct and different finite wavelength band of light wherein the capture of each frame comprises the steps of illuminating the subject scene with a finite wavelength band of light of approximately 10 nm bandwidth or less;

collecting image light from the illuminated subject scene with an objective lens;

splitting, with a beam splitter, the collected image light into a first beam of a first finite wavelength band and a second beam of a second finite wavelength band, wherein the first finite wavelength band does not overlap in wavelength with the second finite wavelength band;

directing the first beam through a first deformable lens and to a first image sensor;

adjusting the focal length of the first deformable lens, such that an image captured by the first image sensor is in-focus;

directing the first beam through a first variable band-pass spectral filter positioned between the beam splitter and the first image sensor;

capturing an in-focus first image of the subject scene illuminated at the finite wavelength band;

transmitting the first captured, in-focus image to the image processor; and storing the in-focus image corresponding to the finite wavelength band;

adjusting the focal length of the second deformable lens, such that a second image captured by a second image sensor is in-focus;

directing the second beam through a second variable band-pass spectral filter positioned between the beam splitter and the second image sensor;

capturing a second in-focus image of the illuminated subject scene with the second image sensor at the second finite wavelength band;

transmitting the captured, second in-focus image to the image processor; and storing the second in-focus image corresponding to the second finite wavelength band; and wherein the capture of the first image is accompanied by the capture of the second image; and wherein the capture of each image comprises the further steps of setting an angular position of the first variable spectral filter, defining thereby a first sub-band of the first finite wavelength band of light falling on the first image sensor; and setting an angular position of the second variable spectral filter, defining thereby a first sub-band of the second finite wavelength band of light falling on the second image sensor.

2. The method of claim 1, wherein the first deformable lens is positioned between the first variable band-pass spectral filter and the first image sensor.

3. The method of claim 1, wherein the first variable band-pass filter causes only a fraction of a spectrum of the wavelength band of illumination light to reach the first image sensor.

4. The method of claim 3, comprising the further step of, after the steps of capturing the first image for a single frame, and capturing the second image for a second single frame, changing the angular position of one of the variable band-pass spectral filters, changing, thereby, the fraction of the spectrum of the wavelength band of illumination light reaching the corresponding sensor.

5. The method of claim 1, wherein the illuminating finite wavelength band of light is changed between each frame, such that the wavelength band for each subsequent does not overlap with previous illuminating wavelengths.

6. The method of claim 4, wherein the illuminating finite wavelength band of light is changed between each frame, such that the wavelength band for each subsequent frame does not overlap with previous illuminating wavelengths.

7. The method of claim 1, wherein the beamsplitter directs light less than 1000 nm along a first optical path and directs light greater than 1000 nm along a second optical path.

* * * * *